United States Patent [19]

Karrer

[11] 4,094,989
[45] June 13, 1978

[54] METHYLENEDIOXY SUBSTITUTED BENZENE DERIVATIVES

[75] Inventor: Friedrich Karrer, Basel, Switzerland

[73] Assignee: Ciba-Geigy Corporation, Ardsley, N.Y.

[21] Appl. No.: 729,055

[22] Filed: Oct. 4, 1976

Related U.S. Application Data

[62] Division of Ser. No. 460,404, Apr. 12, 1974, Pat. No. 3,987,102.

[30] Foreign Application Priority Data

Apr. 18, 1973 Switzerland .................. 5635/73
Mar. 18, 1974 Switzerland .................. 3705/74

[51] Int. Cl.² ............................................. A01N 9/28
[52] U.S. Cl. ............................ 424/282; 260/340.5 R
[58] Field of Search .................. 260/340.5 R; 424/282

[56] References Cited

U.S. PATENT DOCUMENTS 2,825,730  3/1958  Prill ........................... 260/340.5 R
3,988,477  10/1976  Karrer et al. ............... 260/340.5 X

FOREIGN PATENT DOCUMENTS 4,711,063  4/1972  Japan ............................. 424/282

*Primary Examiner*—Ethel G. Love
*Attorney, Agent, or Firm*—Harry Falber

[57] ABSTRACT

Compounds of the formula

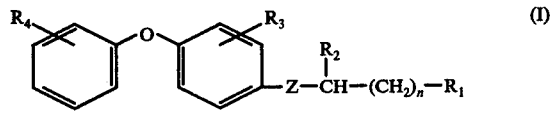

(I)

wherein
n represents the numbers 0 or 1,
Z represents oxygen,

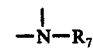

or sulphur
$R_1$ represents the groups

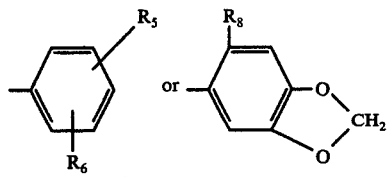

wherein
$R_5$ represents hydrogen, halogen, $C_1$-$C_5$-alkyl, ethynyl, $C_1$-$C_4$-alkylthio, $C_1$-$C_5$-alkoxy, $C_3$-$C_5$-alkenyloxy, $C_3$-$C_5$-haloalkenyloxy, $C_3$-$C_5$-alkynyloxy, nitro, cyano, $C_2$-$C_5$-alkoxycarbonyl, $C_3$-$C_5$-alkenyloxycarbonyl, $C_3$-$C_5$-alkynyloxycarbonyl, $C_1$-$C_3$-alkanoyl, $C_1$-$C_4$-alkylcarbamoyl, (di-$C_1$-$C_4$-alkyl)carbamoyl,
$R_6$ represents hydrogen, halogen, methyl, ethyl, isopropyl or methoxy, and
$R_8$ represents hydrogen or n-propyl,
$R_2$ represents hydrogen, methyl or ethyl,
$R_3$ and $R_4$ each represent hydrogen, methyl, ethyl, methoxy, ethoxy, nitro or halogen, and
$R_7$ represents hydrogen or $C_1$-$C_2$-alkanoyl.

and their use for combating insects and members of the order acarina are disclosed.

12 Claims, No Drawings

METHYLENEDIOXY SUBSTITUTED BENZENE DERIVATIVES

This is a division of application Ser. No. 460,404 filed on Apr. 12, 1974, now U.S. Pat. No. 3,187,102.

The present invention relates to diphenyl ethers, to processes for their preparation, and to their use in pest control.

The said diphenyl ethers have the formula

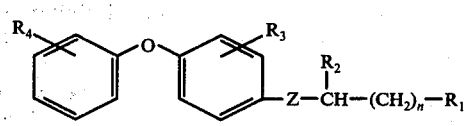

wherein
n represents the numbers 0 or 1,
Z represents oxygen,

or sulphur
$R_1$ represents the groups

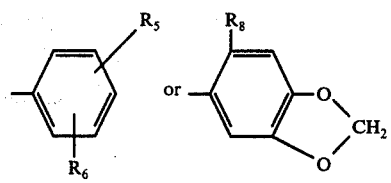

wherein
$R_5$ represents hydrogen, halogen, $C_1$–$C_5$-alkyl, ethynyl, $C_1$–$C_4$-alkylthio, $C_1$–$C_5$-alkoxy, $C_3$–$C_5$-alkenyloxy, $C_3$–$C_5$-haloalkenyloxy, $C_3$–$C_5$-alkynyloxy, nitro, cyano, $C_2$–$C_5$-alkoxycarbonyl, $C_3$–$C_5$-alkenyloxycarbonyl, $C_3$–$C_5$-alkynyloxycarbonyl, $C_1$–$C_3$-alkanoyl, $C_1$–$C_4$-alkylcarbamoyl, (di-$C_1$–$C_4$-alkyl)carbamoyl,
$R_6$ represents hydrogen, halogen, methyl, ethyl, isopropyl or methoxy, and
$R_8$ represents hydrogen or n-propyl,
$R_2$ represents hydrogen, methyl or ethyl,
$R_3$ and $R_4$ each represent hydrogen, methyl, ethyl, methoxy, ethoxy, nitro or halogen, and
$R_7$ represents hydrogen or $C_1$–$C_2$-alkanoyl.

By halogen is meant fluorine, chlorine, bromine or iodine. The alkyl, alkylthio, alkoxy, alkenyloxy, haloalkenyloxy or alkynyloxy groups given under $R_5$ are straight-chain or branched-chain. Examples of such groups are: methyl, ethyl, n-propyl, isopropyl, methylthio, methoxy, ethoxy, allyloxy, β-chloroallyloxy, γ-chloroallyloxy, propargyloxy or 1-butin-3-yloxy. The alkyl, alkoxy, alkenyloxy or alkynyloxy parts of an alkoxycarbonyl, alkenyloxycarbonyl, alkynyloxycarbonyl, or dialkylcarbamoyl group $R_5$ can be branched-chain or straight-chain. Examples of alkoxy, alkenyloxy, alkynyloxycarbonyl or dialkylcarbamoyl groups are: carbomethoxy, carbethoxy, allyloxycarbonyl, propargyloxycarbonyl or diethylcarbamoyl. Examples of alkanoyl groups denoted by $R_5$ and $R_7$ are: formyl, acetyl or propionyl.

Preferred compounds of formula I by virtue of their action are those wherein n represents the number O,
Z represents oxygen or sulphur,
$R_1$ represents the groups

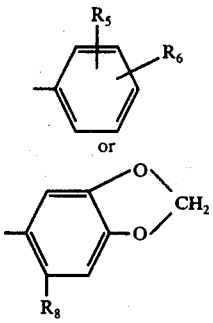

wherein
$R_5$ represents hydrogen, methyl, ethyl, propyl, isopropyl, fluorine, chlorine, bromine, iodine, nitro, methoxy, ethoxy, methylmercapto, propargyloxy, allyloxy, $C_2$–$C_3$-alkoxycarbonyl, propargyloxycarbonyl, acetyl or diethylcarbamoyl,
$R_6$ represents hydrogen, chlorine, methyl, ethyl or methoxy and
$R_8$ represents hydrogen or n-propyl, and
$R_2$ represents hydrogen or methyl and
$R_3$ and $R_4$ each represent hydrogen, chlorine, methyl, methoxy or ethoxy.

The compounds of formula I can be prepared according to the following methods known per se by alkylation of a 4-phenoxyphenol or 4-phenoxyphenolate, of a 4-phenoxythiophenol or 4-phenoxy-thiophenolate or of a 4-phenoxyaniline II or IV with a halide III, in the presence of a base or of an acid-binding agent:

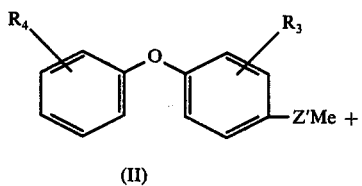

(2) If $R_7$ represents hydrogen:

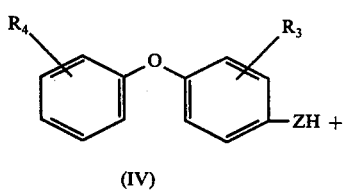

(3) Process for the preparation of compounds of formula I wherein Z = —$NR_7$—, n = O, $R_2$ = H, $R_7$ = hydrogen, formyl or acetyl, and $R_1$, $R_3$ and $R_4$ have the meanings given for formula I:

A primary aromatic amine V is condensed, in a known manner, with an aromatic, optionally substituted aldehyde VI, optionally in the presence of an acid catalyst, such as, e.g. p-toluenesulphonic acid or sulphuric acid, to an azomethine derivative VII, with the separation of water. The —N=C bond of the azomethine VII is hydrogenated, e.g. catalytically in the presence of a metal catalyst, such as, e.g. finely divided nickel, palladium or platinum. The phenoxy-aniline derivative VIII can, if required, be further treated with an acylating agent, such as, e.g. carboxylic acid anhydrides or carboxylic acid chlorides, whereby compounds of formula IX are obtained.

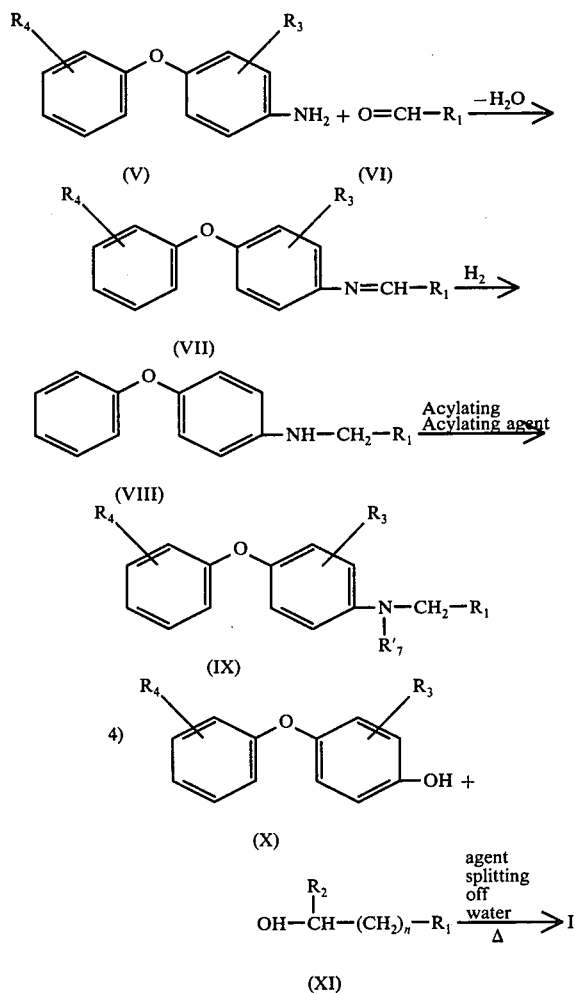

In the above process, condensation of a compound of formula X with a compound of formula XI with catalytic splitting-off of water is performed preferably at a temperature of 60° – 110° C. Dicyclohexylcarbodiimide, for example, can be used as the agent splitting off water.

In formulae II to XI, the symbols $R_1$ to $R_4$ and n have the meanings given for formula I, $R'_7$ stands for formyl or acetyl, Z' for oxygen or sulphur, X for halogen, especially chlorine or bromine, and Me for a metal of the 1st or 2nd main group of the periodic system, particularly sodium, potassium or calcium.

Suitable acid-binding agents or bases are, e.g. tertiary amines such as trialkylamines, pyridine or dialkylanilines; also inorganic bases such as hydrides or hydroxides; and alkoxides and carbonates of alkali metals and alkaline-earth metals. Processes 1 and 2 are performed as a reaction temperature of between −10° and 130° C, preferably between 10° and 80° C, under normal pressure and in the presence of solvents or diluents.

Suitable solvents or diluents are, e.g. ethers such as diethyl ether, diisopropyl ether, 1,2-dimethoxyethane, dioxane or tetrahydrofuran; N,N-dialkylated carboxylic acid amides such as dimethylformamide; aliphatic and aromatic hydrocarbons, particularly benzene, toluene, xylenes or ethylbenzene; ketones such as acetone, methylethyl ketone or cyclohexanone, as well as hexamethylphosphoric acid triamide or dimethylsulphoxide.

The starting materials of formulae II to VI, X and XI are known compounds, or can be prepared by methods analogous to those described in the literature. The azomethines of formula VII are in some cases new compounds.

The compounds of formula I are suitable for the control of insects of the families: Acrididae, Blattidae, Gryllidae, Gryllotalpidae, Tettigoniidae, Cimicidae, Phyrrhocoridae, Reduviidae, Aphididae, Delphacidae, Diaspididae, Pseudococcidae, Chrysomelidae, Coccinellidae, Bruchidae, Scarabaeidae, Dermestidae, Tenebrionidae, Curculionidae, Tineidae, Noctuidae, Lymantriidae, Pyralidae, Galleridae, Culicidae, Tipulidae, Stomoxydae, Muscidae, Calliphoridae, Trypetidae and Pulicidae, as well as acarids of the families: Ixodidae, Argasidae, Tetranychidae and Dermanyssidae.

The insecticidal action of the said compounds can be appreciably widened and adapted to suit given circumstances by the addition of other insecticides and/or acaricides. Suitable additives are, e.g.:
organic phosphorus compounds,
nitrophenols and derivatives,
formamidines, ureas,
carbamates or
chlorinated hydrocarbons.

The compounds of formula I can be used on their own or together with suitable carriers and/or additives. Suitable carriers and additives may be solid or liquid, and they correspond to the substances common in formulation practice, such as, e.g. natural or regenerated substances, solvents, dispersing agents, wetting agents, adhesives, thickeners, binders and/or fertilisers.

For application, the compounds of formula I can be processed into the form of dusts, emulsion concentrates, granulates, dispersions, sprays or solutions, the formulation of these preparations being effected in a manner commonly known in practice.

The agents according to the invention are prepared in a manner known per se by the intimate mixing and/or grinding of active substances of formula I with suitable carriers, optionally with the addition of dispersing agents or solvents which are inert to the active substances. The active substances can be obtained and used in the following forms:

solid preparations:
dusts, scattering agents, granulates, coated granulates, impregnated granulates and homogeneous granulates;

liquid preparations:
(a) water-dispersible active-substance concentrates: wettable powders, pastes or emulsions;
(b) solutions.

The content of active substance in the described agents is between 0.1 and 95%.

The active substances of formula I can be formulated, for example, as follows:

Dusts:

The following substances are used in the preparation of a) a 5% dust, and b) a 2% dust:

| a) | 5 parts of active substance, |
| --- | --- |
|    | 95 parts of talcum; |
| b) | 2 parts of active substance, |
|    | 1 part of highly dispersed silicic acid, |
|    | 97 parts of talcum. |

The active substances are mixed and ground with the carriers.

Granulate:

The following substances are used to prepare a 5% granulate:

| 5 | parts of active substance, |
| --- | --- |
| 0.25 | part of epichlorhydrin, |
| 0.25 | part of cetyl polyglycol ether, |
| 3.50 | parts of polyethylene glycol, |
| 91 | parts of kaolin (particle size 0.3–0.8 mm). |

The active substance is mixed with epichlorhydrin and dissolved with 6 parts of acetone; the polyethylene glycol and cetyl polyglycol ether are then added. The solution thus obtained is sprayed onto kaolin, and the acetone subsequently evaporated off in vacuo.

Wettable powder:

The following constituents are used for the preparation of a) a 40%, b) and c) a 25%, and d) a 10% wettable powder:

| a) | 40 | parts of active substance, |
| --- | --- | --- |
|    | 5 | parts of sodium lignin sulphonate, |
|    | 1 | part of sodium dibutyl-naphthalene sulphonate, |
|    | 54 | parts of silicic acid; |
| b) | 25 | parts of active substance, |
|    | 4.5 | parts of calcium lignin sulphonate, |
|    | 1.9 | parts of Champagne chalk/hydroxyethyl cellulose mixture (1:1), |
|    | 1.5 | parts of sodium dibutyl naphthalene sulphonate, |
|    | 19.5 | parts of silicic acid, |
|    | 19.5 | parts of Champagne chalk, |
|    | 28.1 | parts of kaolin; |
| c) | 25 | parts of active substance, |
|    | 2.5 | parts of isooctylphenoxy-polyoxyethylene-ethanol, |
|    | 1.7 | parts of Champagne chalk/hydroxyethyl cellulose mixture (1:1), |
|    | 8.3 | parts of sodium aluminium silicate, |
|    | 16.5 | parts of kieselguhr, |
|    | 46 | parts of kaolin; |
| d) | 10 | parts of active substance, |
|    | 3 | parts of a mixture of the sodium salts of saturated fatty alcohol sulphates, |
|    | 5 | parts of naphthalenesulphonic acid/formaldehyde condensate, |
|    | 82 | parts of kaolin. |

The active substances are intimately mixed, in suitable mixers, with the additives, the mixture being then ground in the appropriate mills and rollers. Wettable powders are obtained which can be diluted with water to give suspensions of any desired concentration.

Emulsifiable concentrates:

The following substances are used to prepare a) a 10% and b) a 25% emulsifiable concentrate:

| a) | 10 | parts of active substance, |
| --- | --- | --- |
|    | 3.4 | parts of epoxidised vegetable oil, |
|    | 3.4 | parts of a combination emulsifier consisting of fatty alcohol polyglycol ether and alkylarylsulphonate calcium salt, |
|    | 40 | parts of dimethylformamide, |
|    | 43.2 | parts of xylene; |
| b) | 25 | parts of active substance, |
|    | 2.5 | parts of epoxidised vegetable oil, |
|    | 10 | parts of an alkylarylsulphonate/fatty alcohol polyglycol ether mixture, |
|    | 5 | parts of dimethylformamide, |
|    | 57.5 | parts of xylene. |

From these concentrates it is possible to prepare, by dilution with water, emulsions of any desired concentration.

Spray:

The following constituents are used to prepare a 5% spray:

| 5 parts of active substance, |
| --- |
| 1 part of epichlorhydrin, |
| 94 parts of ligroin (boiling limits 160–190° C). |

EXAMPLE 1

(A) Preparation of 1-phenoxy-4-(3',4'-methylenedioxy)-benzyloxybenzene 18 g of finely powdered anhydrous potassium carbonate is added to a solution of 18.6 g of 4-hydroxy-diphenyl ether in 100 ml of anhydrous acetone, and the mixture heated to the reflux temperature of the acetone. After half an hour, the solution of 17.1 g of 3,4-methylenedioxychloromethylbenzene in 100 ml of toluene is added dropwise within one hour, and the reaction mixture refluxed for a further 18 hours. The reaction solution is then filtered off from the solid phase, and the solvent completely removed in vacuo from the filtrate. The residue is dissolved in acetic acid ethyl ester/toluene, ca. 1:1; the solution is repeatedly washed with ice-cold 10% potassium hydroxide solution and afterwards with water and saturated sodium chloride solution until neutral. After drying of the organic phase by means of sodium sulphate, the solvent is completely removed in vacuo, and the residue, solidifying in crystalline form, recrystallised twice in acetonitrile to obtain 1-phenoxy-4-(3',4'-methylenedioxy)-benzyloxybenzene, M.P. 90° – 91° C.

(B) Preparation of 4-phenoxy-N-(3,4-methylenedioxybenzyl)-aniline

The solution of 47.6 g of 4-phenoxy-(3,4-methylenedioxybenzylidene)-aniline in 500 ml of pure methanol and 450 ml of methylcellosolve is, after the addition of 3 g of platinum oxide, catalytically hydrogenated at 20°– 30° C to effect the absorption of 3.36 l of hydrogen. The catalyst is filtered off, and the solvent removed in vacuo from the filtrate. The residue is chromatographically purified through silica gel (eluant: ether/hexane 1:1), and the resulting pure 4-phenyl-N-(3,4-methylenedioxybenzyl)-aniline recrystallised in ether/hexane, M.P. 95° – 96° C.

The starting material used for catalytic hydrogenation, 4-phenoxy-(3,4-methylenedioxy-benzylidene)-aniline, is prepared as follows: the solution of 75 g of 3,4-methylenedioxy-benzaldehyde (piperonal) and 92.5 g of 4-aminodiphenyl ether in 500 ml of benzene is refluxed, with separation of water, for 8 hours. After the water has been completely separated, the reaction mixture is concentrated by evaporation; the crystals precipitated after cooling to about + 5° C are filtered off under suction; the crystal mass is recrystallised firstly in anhydrous benzene and subsequently in acetonitrile to thus obtain pure 4-phenoxy-(3,4-methylenedioxyben-zylidene)-aniline, M.P. 89° - 91° C. The following azomethine derivatives are prepared in a manner analogous to that described above:

of 4-phenoxy-N-(3,4-methylenedioxybenzyl)-aniline and 6 g of N-ethyl-diisopropylamine in 100 ml of anhydrous benzene. The whole is subsequently heated to room temperature and stirred for a further 8 hours. The precipitated N-ethyl-diisopropylamine-hydrochloride is

| Compounds | Physical data |
|---|---|
| [structure: phenoxy-phenyl-N=CH-phenyl-O-CH₂-C≡CH] | M.P.: 76 – 77° C |
| [structure: phenoxy-phenyl-N=CH-phenyl-CH₃] | M.P.: 79 – 80° C |
| [structure: phenoxy-phenyl-N=CH-phenyl-Cl] | M.P.: 104 – 106° C |
| [structure: 4-chlorophenoxy-phenyl-N=CH-(3,4-methylenedioxy)phenyl] | M.P.: 120 – 121° C |

(C) Preparation of 4-phenoxy-N-acetyl-N-(3,4-methylenedioxybenzyl)-aniline 3.2 ml of acetyl chloride dissolved in 10 ml of anhydrous benzene is added dropwise at 0° - 5° C in the course of one hour, with stirring, to a solution of 12.7 g separated by filtration; the filtrate is washed with 10% sodium carbonate solution and then with water. After drying of the organic phase by means of sodium sulphate, the benzene is distilled off in vacuo, and the residue recrystallised in hexane to obtain 4-phenoxy-N-acetyl-N-(3,4-methylenedioxybenzyl)-aniline, M.P. 75°- 76° C.

Table 1

The following further compounds are prepared in a manner analagous to that previously described:

| Compounds | Physical data |
|---|---|
| [structure: phenoxy-phenyl-O-CH₂-phenyl-C₂H₅] | M.P. 55 – 57° C |
| [structure: phenoxy-phenyl-O-CH₂-phenyl(o-C₂H₅)] | $n_D^{20} = 1,5840$ |
| [structure: phenoxy-phenyl-O-CH₂-phenyl-CH₃] | M.P.: 69 – 70° C |
| [structure: phenoxy-phenyl-O-CH₂-phenyl-NO₂] | M.P.: 126 – 128° C |
| [structure: phenoxy-phenyl-O-CH₂-phenyl-Cl] | M.P.: 71 – 72° C |

Table 1-continued
The following further compounds are prepared in a manner analagous to that previously described:
| Compounds | Physical data |
|---|---|
| 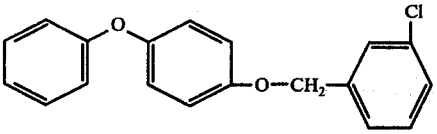 | M.P.: 60 – 61° C |
| 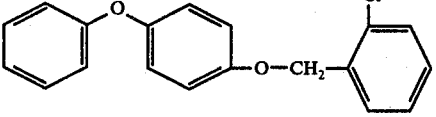 | $n_D^{20} = 1{,}6003$ |
| 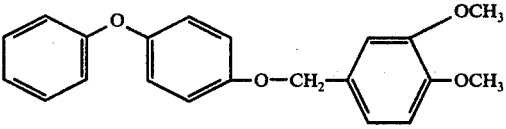 | M.P.: 107 – 109° C |
| 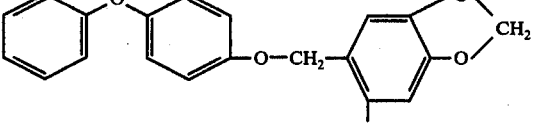 | $n_D^{20} = 1{,}5801$ |
| 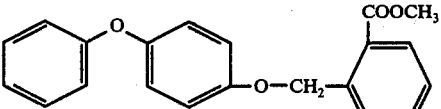 | M.P.: 60 – 62° C |
| 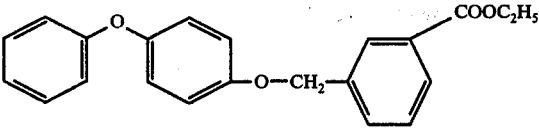 | M.P.: 45 – 47° C |
| 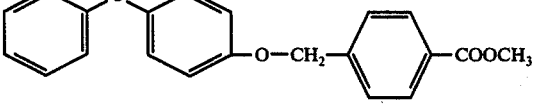 | M.P.: 108 – 109° C |
| 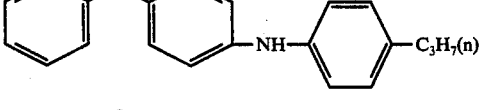 | M.P.: 65 – 67° C |
| 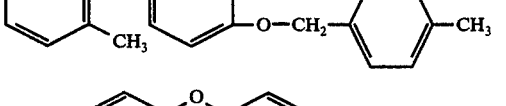 | M.P.: 60 – 61° C |
| 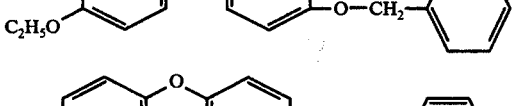 | M.P.: 103 – 104° C |
| 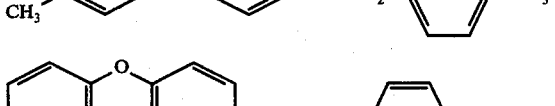 | M.P.: 97 – 98° C |
|  | M.P.: 50 – 51° C |

Table 1-continued

The following further compounds are prepared in a manner analagous to that previously described:

| Compounds | Physical data |
|---|---|
| Ph-O-C₆H₄-NH-CH₂-C₆H₄-Cl | $n_D^{20} = 1.6313$ |
| 4-CH₃-C₆H₄-O-C₆H₄-O-CH₂-C₆H₄-Cl | M.P.: 112 – 113° C |
| Ph-O-C₆H₄-O-CH₂-C₆H₄-OCH₃ | M.P.: 94 – 95° C |
| Ph-O-C₆H₄-O-CH₂-CH₂-Ph | M.P.: 43 – 45° C |
| Ph-O-C₆H₄-O-CH₂-Ph | M.P.: 68 – 69° C |
| Ph-O-C₆H₄-O-CH₂-C₆H₄(CH₃) | M.P.: 55 – 56° C |
| Ph-O-C₆H₄-S-CH₂-C₆H₄-CH₃ | M.P.: 61 – 62° C |
| Ph-O-C₆H₄-O-CH₂-C₆H₃(Cl)(Cl) | M.P.: 89 – 90° C |
| Ph-O-C₆H₄-O-CH₂-C₆H₄-F | M.P.: 74 – 75° C |
| Ph-O-C₆H₄-O-CH₂-C₆H₄-Br | M.P.: 81 – 83° C |
| Ph-O-C₆H₄-O-CH₂-C₆H₄-COCH₃ | M.P.: 90 – 91° C |
| Ph-O-C₆H₄-S-CH₂-C₆H₃(O-CH₂-O) | M.P.: 44 – 45° C |
| Ph-O-C₆H₄-O-CH₂-C₆H₄-J | M.P.: 90 – 91° C |

Table 1-continued
The following further compounds are prepared in a manner analagous to that previously described:
| Compounds | Physical data |
|---|---|
| 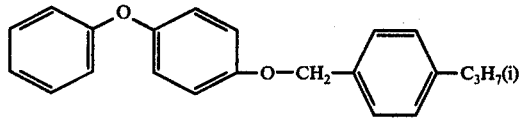 | M.P.: 66 – 67° C |
| 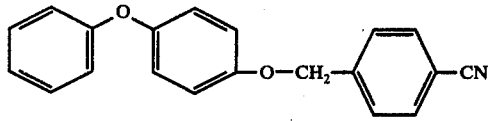 | M.P.: 103 – 105° C |
| 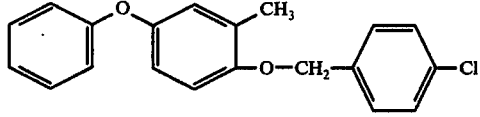 | M.P.: 45 – 46° C |
| 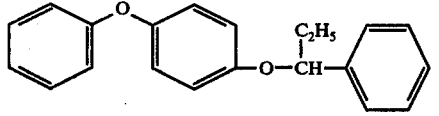 | $n_D^{20}$: 1,5858 |
| 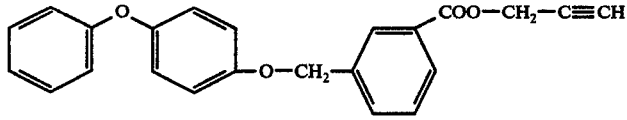 | $n_D^{20}$ = 1,5988 |
| 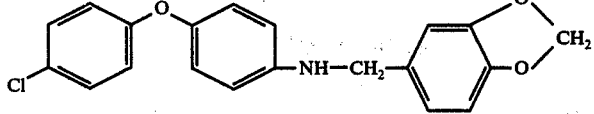 | M.P.: 112 – 113° C |
| 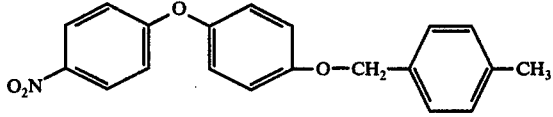 | M.P.: 133 – 134° C |
| 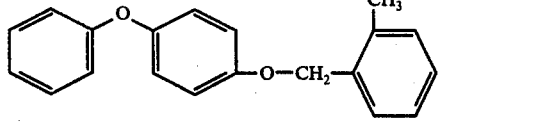 | M.P.: 41 – 43° C |
| 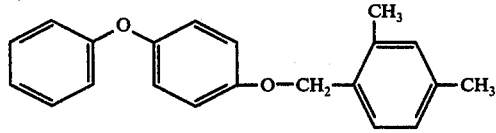 | M.P.: 59 – 60° C |
| 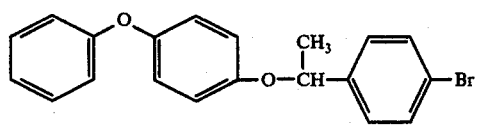 | $n_D^{20}$ = 1,6064 |
| 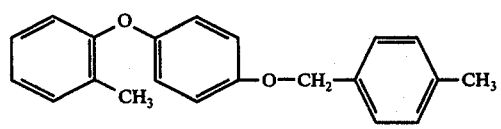 | M.P. 60 – 61° C |
| 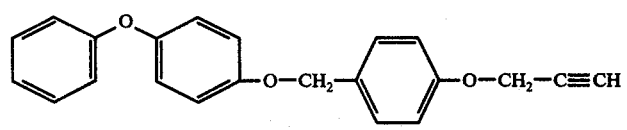 | M.P.: 92 – 93° C |
| 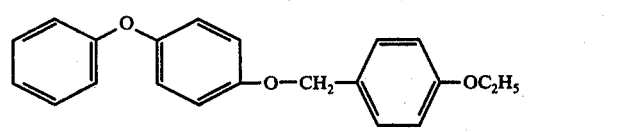 | M.P.: 79 – 80° C |

Table 1-continued

The following further compounds are prepared in a manner analagous to that previously described:

| Compounds | Physical data |
|---|---|
| Ph-O-C6H4-O-CH2-C6H4-SCH3 | M.P. 90 – 91° C |
| Ph-O-C6H4-O-CH2-C6H4(OCH3) (meta-OCH3) | $n_D^{20} = 1.5972$ |
| Ph-O-C6H4-O-CH(CH3)-C6H4-OCH3 | $n_D^{20} = 1.5778$ |
| Ph-O-C6H3(CH3)-O-CH2-(methylenedioxyphenyl) | |
| Ph-O-C6H4-O-CH(CH3)-C6H4-CH3 | M.P.: 76 – 77° C |
| Ph-O-C6H4-S-CH2-C6H4-O-CH2-C≡CH | |
| Ph-O-C6H4-O-CH2-C6H3(NO2)(Cl) | |
| Ph-O-C6H4-O-CH(CH3)-(methylenedioxyphenyl) | |
| (2-CH3-C6H4)-O-C6H4-O-CH2-(methylenedioxyphenyl) | |
| (3-CH3-C6H4)-O-C6H4-O-CH2-(methylenedioxyphenyl) | |
| (3-CH3-C6H4)-O-C6H4-O-CH2-C6H4-CH3 | |
| (4-O2N-C6H4)-O-C6H4-O-CH2-(methylenedioxyphenyl) | M.P.: 142 – 144° C |

Table 1-continued

The following further compounds are prepared in a manner analagous to that previously described:

| Compounds | Physical data |
|---|---|
| [phenyl-O-phenyl-O-CH$_2$-phenyl-CON(C$_2$H$_5$)$_2$] | $n_D^{20}$: 1,5893 |
| [phenyl-O-phenyl-O-CH$_2$-phenyl-O-CH$_2$-CH=CHCl] | |
| [phenyl-O-phenyl-O-CH$_2$-phenyl-OCH$_2$-CH=CH$_2$] | |

EXAMPLE 2

(A) Contact action on Dysdercus-fasciatus larvae

A specific amount of a 0.1% acetonic active-substance solution (corresponding to 10 mg of active substance per square meter) was transferred by pipet to an aluminium dish and uniformly distributed. After evaporation of the acetone, 10 larvae in the 5th stage of Dysdercus fasciatus were placed into the treated dish containing feed and moist cotton wool. The dish was then covered with a perforated lid. After about 10 days, i.e. as soon as the control insects had moulted into adults, the test insects were examined to determine the number of normal adults.

Compounds according to Example 1 and Table 1 exhibited a good action in the above test.

(B) Contact action on Aedes-aegypti larvae

About 20 two-day-old larvae of the yellow-fever mosquito (Aedes aegypti) were placed in position in a beaker containing a solution of the active substance (concentration 5 ppm). The beaker was then covered with a perforated lid. After the control insects had moulted into adults, the test insects were examined and the percentage of normal adults in comparison with the control adults determined.

Compounds according to Example 1 and Table 1 exhibited a good action in the above test.

(C) Contact action on Tenebrio-molitor pupae

A specific amount of a 0.1% acetonic active-substance solution corresponding to 10 mg of active substance per square meter was transferred by pipet into an aluminium dish and uniformly distributed. After evaporation of the acetone, 10 freshly formed pupae were placed on the treated surface, and the dish covered with a perforated lid. After the control insects had left the cocoon as imagines, the test insects were examined to determine the number of normal adults.

Compounds according to Example 1 and Table 1 exhibited a good action in the above test.

EXAMPLE 3

(A) Action against Musca domestica

An amount in each case of 50 g of CSMA maggot substrate was weighed off in beakers. For each active substance, 2.5 ml of a 1% acetonic solution in the respective substance was transferred twice to 50 g of maggot substrate each time. After a thorough mixing of the treated substrate, the solvent was allowed to evaporate off. There were then deposited per active substance in each case 25 one-, two- and three-day-old maggots and about 50 fly eggs. After completion of pupation, the pupae were flushed out and counted. After a period of ten days, the number of emerged flies was determined and hence any effect on metamorphosis established.

Compounds according to Example 1 and Table 1 exhibited in this test a good action against Musca domestica.

(B) Action against Ephestia kuhniella 50 g of wheat flour was made up in two beakers with a specific amount of active substance to give a 5% dust, the concentration thus being 0.05%. Into each beaker (25 g of flour) were placed 10 larvae of Ephestia kuhniella. The course of population was ascertained over a period of 8 weeks and the number of moths determined.

Compounds according to Example 1 and Table 1 exhibited a good action in the test against Ephestia kuhniella.

EXAMPLE 4

Action against red spider mites

Phaseolus vulgaris (bush beans) were infested, 12 hours before the test for acaricidal action, with an infested piece of leaf from a mass culture of Tetranychus urticae. The tranferred mobile stages were sprayed with the emulsified test preparations, at a concentration of 0.04%, by means of a chromatography-sprayer in a manner ensuring no running off of the spray liquor. An assessment was made after 2 to 7 days, by examination under a binocular, of the living and of the dead larvae, adults and eggs, and the results expressed in percentages. The treated plants were kept during the holding time in greenhouse compartments at 25° C.

The compounds according to Example 1 and Table 1 exhibited in the above test a good action against eggs, larvae and adults of Tetranychus urticae.

What we claim is:
1. A compound of the formula

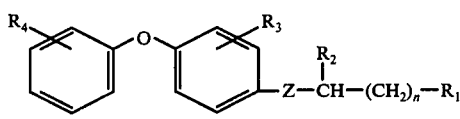 (I)

wherein
n represents the numbers 0 or 1,
Z represents oxygen,

or sulphur,
R₁ represents

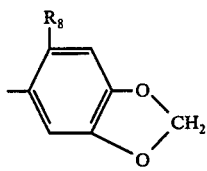

R₈ represents hydrogen or n-propyl,
R₂ represents hydrogen, methyl or ethyl,
R₃ and R₄ each represent hydrogen, methyl, ethyl, methoxy, ethoxy, nitro or halogen, and
R₇ represents hydrogen or $C_1-C_2$-alkanoyl.

2. The compound according to claim 1 wherein
n represents the number 0,
Z represents oxygen or sulphur,
R₁ represents

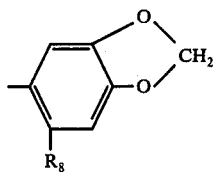

wherein
R₈ represents hydrogen or n-propyl,
R₂ represents hydrogen or methyl, and
R₃ and R₄ each represent hydrogen, chlorine, methyl, methoxy or ethoxy.

3. 1-Phenoxy-4-[(3',4'-methylenedioxy)-benzyloxy]-benzene according to claim 2.

4. 1-Phenoxy-4-[(2'-n-propyl-3',4'-methylenedioxy)-benzyloxy]benzene according to claim 2.

5. 4-Phenoxy-1[(3',4'-methylenedioxy)-benzyl]-aniline according to claim 1.

6. 1-Phenoxy-4-[(3',4'-methylenedioxy)-benzylthio-]benzene according to claim 2.

7. 5-Phenoxy-2-[(3',4'-methylenedioxy)-benzyloxy]-toluene according to claim 2.

8. 1-Phenoxy-4-[(α-methyl-3',4'-methylenedioxy)-benzyloxy]benzene according to claim 2.

9. 1-(2'-Toluyloxy)-4-[(3',4'-methylenedioxy)-benzyloxy]-benzene according to claim 2.

10. 1-(3'-Toluyloxy)-4-[(3',4'-methylenedioxy)-benzyloxy]-benzene according to claim 2.

11. An insecticidal or acaricidal agent containing an insecticidal or acaricidal effective amount of a compound of claim 1 together with a suitable carrier therefor.

12. A method for the control of insects or members of the order Acarina which comprises applying to the locus thereof an insecticidal or acaricidal effective amount of a compound of claim 1.

* * * * *